(12) United States Patent
Moon et al.

(10) Patent No.: US 7,453,017 B2
(45) Date of Patent: Nov. 18, 2008

(54) PALLADIUM-BASED CATALYST FOR SELECTIVE HYDROGENATION OF ACETYLENE

(75) Inventors: Sang Heup Moon, Seoul (KR); Woo Jae Kim, Seoul (KR); Jung Hwa Kang, Seoul (KR); In Young Ahn, Seoul (KR)

(73) Assignee: BASF AG, Ludwigshafen (DE)

( * ) Notice: Subject to any disclaimer, the term of this patent is extended or adjusted under 35 U.S.C. 154(b) by 356 days.

(21) Appl. No.: 10/549,774

(22) PCT Filed: Mar. 26, 2004

(86) PCT No.: PCT/EP2004/003263

§ 371 (c)(1),
(2), (4) Date: Sep. 19, 2005

(87) PCT Pub. No.: WO2004/085353

PCT Pub. Date: Oct. 7, 2004

(65) Prior Publication Data

US 2006/0229478 A1    Oct. 12, 2006

(30) Foreign Application Priority Data

Mar. 26, 2003   (KR) ............... 10-2003-0018888
Mar. 26, 2003   (KR) ............... 10-2003-0018890
Mar. 26, 2003   (KR) ............... 10-2003-0018891
Mar. 27, 2003   (KR) ............... 10-2003-0019039

(51) Int. Cl.
*C07C 5/09*     (2006.01)
*B01J 21/06*    (2006.01)
*B01J 23/04*    (2006.01)
*B01J 23/10*    (2006.01)
*B01J 23/44*    (2006.01)
*B01J 23/58*    (2006.01)
*B01J 23/63*    (2006.01)

(52) U.S. Cl. ............... 585/277; 502/262; 502/303; 502/330; 585/259; 585/262

(58) Field of Classification Search ............... 502/303, 502/232, 262, 330; 585/259, 262, 277
See application file for complete search history.

(56) References Cited

U.S. PATENT DOCUMENTS

| | | | |
|---|---|---|---|
| 3,325,556 | A | 6/1967 | DeRosset et al. |
| 4,387,258 | A | 6/1983 | Vadekar et al. |
| 4,829,329 | A | 5/1989 | Toyoda et al. |

(Continued)

FOREIGN PATENT DOCUMENTS

KR    2000-0059743    10/2000

OTHER PUBLICATIONS

Moon, S. H. et al., "Selective Hydrogenation of Acetylene on Pd/SiO$_2$ Catalysts Promoted with Ti, Nb and Ce Oxides", Catalysis Today 63 (2000), p. 183-188.

(Continued)

*Primary Examiner*—Vickie Kim
*Assistant Examiner*—Brittany M Martinez
(74) *Attorney, Agent, or Firm*—Connolly Bove Lodge & Hutz LLP (57) ABSTRACT

The present invention describes a Pd-catalyst which further contains La, Ti, Nb, K or Si. The Pd-catalyst has a high ethylene selectivity even after a low temperature reduction in the selective hydrogenation of acetylene to ethylene. The invention also relates to the production of the catalyst. A catalyst of the invention consists essentially of 0.05 to 2.0% by weight, based on the supported catalyst, of palladium and one or two metals chosen form the group consisting of lanthanum, niobium, titanium, potassium and silicon. The catalyst can be prepared by the following procedure.
(1) Impregnating a support in aqueous solution of tetra amine palladium hydroxide, followed by drying and calcination;
(2) The second and, if necessary, a third metal is impregnated by impregnating the Pd-catalyst in the solution of the metal precursor followed by drying and calcination;
(3) The catalyst according to step (2) is then reduced in hydrogen at 200° C. to 600° C. for 1 to 5 hours.

13 Claims, 5 Drawing Sheets

U.S. PATENT DOCUMENTS

| | | |
|---|---|---|
| 4,906,800 A | 3/1990 | Henry et al. |
| 6,413,905 B1 | 7/2002 | Meyer et al. |
| 2002/0165092 A1 | 11/2002 | Zhang et al. |

OTHER PUBLICATIONS

Shin, E. W. et al., "Performance of Si-modified Pd Catalyst in Acetylene Hydrogenation: The Origin of the Ethylene Selectivity Improvement", Applied Catalysis A: General 223 (2002), pp. 161-172.

Bond, G. C., "Catalysis by Metals", Academic Press, London and New York, 1962, pp. 281-309.

Lam, W. K. et al., "Catalyst Aids Selective Hydrogenation", The Oil and Gas Journal (1972), pp. 66-70.

PALLADIUM-BASED CATALYST FOR SELECTIVE HYDROGENATION OF ACETYLENE

RELATED APPLICATIONS

This application is a national stage application (under 35 U.S.C. 371) of PCT/EP2004/003263 filed Mar. 26, 2004 which claims benefit to Korean applications 2003/18888, 2003/18890, and 2003/18891 filed Mar. 26, 2003 and Korean application 2003/19039 filed Mar. 27, 2003.

FIELD OF INVENTION

The invention concerns Pd-based, supported catalysts and the production of same particularly for use in the selective hydrogenation of acetylene to ethylene.

BACKGROUND OF THE INVENTION

The ethylene stream from the overhead of a deethanizer unit in a naphta cracker contains about 0.5 to 2.0% by weight of acetylene which is a poison in the ensuing process of ethylene polymerisation, so that the ethylene impurities should be lowered to below 5 ppm. Selective hydrogenation is a common method to remove acetylene in the stream. Two factors are important in this process. One is the ethylene selectivity, i.e. the fraction of acetylene produced by acetylene conversion, and the other is the catalyst lifetime which is limited by green-oil deposition during reaction.

For the selective hydrogenation of acetylene to ethylene, noble metal supported catalysts are usually used and especially, palladium-based catalyst is known to show high activity and high ethylene selectivity.

According to Bond et al. the ethylene selectivity on transition metals is lowered in the sequence of Pd>Rh, Pt>Ni>>Ir ("Catalysis by metals", Academic Press, New York, 281-309, 1962).

A catalyst preparation method for impregnating palladium on silica is presented in U.S. Pat. No. 4,387,258 and a catalyst preparation method of palladium/titania is presented in U.S. Pat. No. 4,829,329.

Besides silica and titania, alumina is also commercially used as a support for catalysts used in acetylene hydrogenation. These supported catalysts are easily deactivated by the formation of green oil, which is a side reaction occurring on the support surface. This green oil blocks the pores and covers the active sites, so that the phenomenon shortens the regeneration cycle and catalyst lifetime.

In the acetylene hydrogenation, ethylene selectivity as well as catalyst lifetime is important.

According to Bond and Well, the reason for why acetylene is selectively hydrogenated, despite the fact that the hydrogenation rate of ethylene is faster by 10 to 100 times than that of acetylene, is because the adsorption strength of acetylene is much stronger than that of ethylene. Hence acetylene hydrogenation is dominant when there is a competition of hydrogenation between acetylene and ethylene. So the reaction on the catalyst is determined largely by the rate of adsorption and desorption instead of the rate of surface reaction. According to the analysis of the property of the 8B transition metals, including Pd, for the adsorption of acetylene, ethylene or propylene, the rate of adsorption decreased in the following order and the rate of desorption decreased in the reverse order. Acetylene>Diolefin>Olefin>Paraffin (The Oil and Gas Journal, 27, 66 (1972)).

Therefore, if we add diolefin as an additive to the reactant stream of acetylene hydrogenation, we can suppress the adsorption of ethylene and consequently, can selectively hydrogenate acetylene to ethylene. This diolefin, which has adsorption strength stronger than that of ethylene and weaker than that of acetylene, is called as a moderator. But the diolefin itself induces the green oil formation, and furthermore, a separation of unreacted diolefin after acetylene hydrogenation is difficult. For this reason, carbon monoxide, which also acts as a moderator in acetylene hydrogenation, is preferred.

A method to increase ethylene selectivity by carbon monoxide is presented in U.S. Pat. No. 3,325,556 and No. 4,906,800. But, carbon monoxide also enhances the formation of green oil by carbonylation reaction, thus, the problem of catalyst regeneration cycle and catalyst lifetime still exists.

Titanium promoter was proposed as an additive to solve the catalyst deactivation problem in acetylene hydrogenation, and the detail is presented in Korean patent No. 2000-0059743. When palladium catalyst is modified with titanium species and reduced at high temperatures, such as 500° C., titanium oxide species is partially reduced and migrates onto the Pd surface and electron is transferred from titanium oxide to palladium, making palladium an electron rich surface. This is called a Strong Metal-Support Interaction (SMSI). The SMSI phenomenon increases the ethylene selectivity, and retards the catalyst deactivation. But, the highest ethylene selectivity of Pd—Ti-catalyst in the experimental condition described in the patent is about 90%, which still needs further improvement.

For the Strong Metal-Support interaction between Ti and Pd to occur, high temperature reduction, such as 500° C., is necessary, but the maximum temperature, which can be elevated inside the industrial reactor, is about 300° C., therefore, the improvement of ethylene selectivity by titanium is limited in the industrial process.

SUMMARY OF THE INVENTION

Therefore, a new catalyst, which exhibit SMSI phenomenon at relatively low temperatures, is needed.

It is an object of the present invention to provide new catalysts, which have high ethylene selectivity in a process for hydrogenation of acetylene even after reduction at lower temperatures in the catalyst preparation or in the catalyst regeneration step, and the production method of the same.

This object is achieved by the use of Pd-based catalysts containing beside palladium lanthanum, lanthanum and silicon, niobium as well as titanium and potassium.

The present invention provides new catalysts and production method of same, which have high ethylene selectivity even after reduction at low temperatures in the catalyst preparation or in the catalyst regeneration step, and a production method of same.

The new catalysts of the invention comprise beside palladium titanium and potassium, lanthanum, lanthanum and silicon or niobium. The palladium catalysts according to the present invention consist of a support and from 0.05 to 2.0% by weight, based on the supported catalyst, of palladium and from 0.035 to 5.2% by weight, based on the supported catalyst, of lanthanum, or from 0.05 to 2.0% by weight, based on the supported catalyst, of palladium, from 0.02 to 1.0% by weight, based on the supported catalyst, of titanium and from 0.0002 to 7.4% by weight, based on the supported catalyst, of potassium, or from 0.05 to 2.0% by weight, based on the supported catalyst, of palladium and from 0.045 to 1.8% by weight, based on the supported catalyst, of niobium, or from 0.05 to 2.0% by weight, based on the supported catalyst, of palladium, from 0.035 to 5.2% by weight, based on the supported catalyst, of lanthanum and from 0.0001 to 0.065% by weight, based on the supported catalyst, of silicon.

The rest of the catalyst is the support.

The above Pd-based hydrogenation catalyst is prepared by the following process:

(1) Pd impregnation procedure by impregnating a support in tetra amine palladium hydroxide aqueous solution followed by drying and calcination and impregnating the support with precursor solutions containing precursors of the further metals;

(2) Ti, Nb or La impregnation procedure, wherein the Pd—La—, Pd—Ti— or Pd—Nb-catalyst is prepared by impregnating the Pd-catalyst in corresponding precursor solution followed by drying and calcination;

(3) If necessary, K impregnation procedure, wherein a Pd—Ti—K-catalyst is prepared by impregnating the Pd—Ti-catalyst in potassium precursor solution followed by drying and calcination;

or if necessary, Si deposition procedure, wherein a Pd—La—Si-catalyst is prepared by Si-CVD (CVD=chemical vapour deposition) on a Pd—La-catalyst, pre-reduced at 350-700° C., followed by oxidation at room temperature;

(4) Reduction procedure wherein the producing of the catalysts includes the reduction process at 300-600° C. for 1-5 hours.

DETAILED DESCRIPTION OF THE INVENTION

In the following, the catalyst preparation is described in more detail:

(1) describes the preparation method of Pd-catalyst. The loaded amount of palladium on the catalyst is adjusted to 0.05-2.00% by weight. A support (Silica, Titania, Alumina etc.) is added to a solution of tetra amine palladium hydroxide $(NH_3)_4Pd(OH)_2$ in water, stirred for 12 hours and washed with distilled water. The catalyst was then dried at 50-150° C. overnight and calcinated in air at 300-700° C. for 1-5 hours.

(2) describes the preparation method of Pd—Ti, Pd—La or Pd—Nb catalyst by impregnating Ti, La or Nb on Pd catalyst, wherein the La-precursor is lanthanum nitrate hydrate dissolved in water, the niobium precursor is tetrakisniobium dissolved in water or hexane and the titanium precursor is chosen from a group consisting of $Ti(O-iPr)_2(DPM)_2$, titanium ethoxide, titanium oxide acetylacetonate and titanium butoxide, each dissolved in water or hexane. 0.02-1.0% by weight of titanium, 0.035-5.2% by weight of lanthanum or 0.045-1.8% by weight, in each case based on the supported catalyst, niobium is loaded on the catalyst.

(3) describes the preparation method of Pd—Ti—K catalyst by impregnating potassium on Pd—Ti catalyst using potassium precursor dissolved in water. The amount of potassium is adjusted to 0.0002-7.4% by weight and the K-precursor is potassium nitrate. After potassium impregnation, the catalyst was dried at 50-150° C. overnight and calcinated in air at 300-500° C. for 1-5 hours. During the calcination process, potassium titanate which is compound of potassium and titanium is formed.

Furthermore (3) describes the Si—CVD procedure on Pd—La catalyst made in step (2). Pd—La catalyst is pre-reduced at 350-700° C. prior to the Si-CVD. In the pre-reduction procedure, La-oxide is partially reduced and migrates onto the Pd surface, consequently, modifies Pd surface. The Si-precursor is chosen from the group consisting of tetrahydrosilane, triethylsilane, tripropylsilane and phenylsilane. The precursor is delivered to the catalyst by carrier gas, such as $H_2$ at 200-300° C.

(4) describes a reduction procedure of the catalyst which is made in step (3). The catalyst is reduced at 300-600° C. for 1-5 hours. Silicon which was deposited through step (3) maintains the interaction of La and Pd even after the catalyst is exposed to air and reduced at low temperatures.

Furthermore the present invention concerns a continuous process for the selective hydrogenation of acetylene to ethylene in the presence of a catalyst according to the present invention, wherein 0.5 to 2.0% by weight of acetylene in ethylene/acetylene gas mixture is used, the reaction temperature is 30 to 120° C. and the flow rate of the gas mixture is 200 to 2500 ml/min×g catalyst.

In addition the present invention concerns the use of a palladium catalyst according to the present invention in the selective hydrogenation of acetylene.

EXAMPLES

Example 1

In Accordance with the Invention—Catalyst A

A. Preparation of Pd catalyst $Pd/SiO_2$ catalyst was prepared by a literature method. 20 g of Silica (JRC-SIO-6, BET surface area: 109 m²/g) were impregnated with 200 ml solution of 0.33% by weight $Pd(NH_3)_4(OH)_2$ and the solution was stirred for 12 hours, and centrifuged and washed with distilled water. The catalyst was then dried at 100° C. for 12 hours and calcinated in air at 300° C. for 2 hours. 1% by weight $Pd/SiO_2$ catalyst was obtained.

B. Ti impregnation

Ti-modified Pd catalysts were prepared by impregnating 1% by weight $Pd/SiO_2$ with hexane solution of diisopropoxide dipivaloylmethanato titanium $(Ti(O-iPr)_2(DPM)_2$; $Pr=C_3H_6$, $DPM=C_{11}H_{19}O_2)$. The catalyst was then dried at 100° C. for 3 hours and calcinated in air at 300° C. for 2 hours.

Hexane solution was made with 150 mg diisopropoxide dipivaloylmethanato titanium in 10 g hexane. The atomic ratio of Ti/Pd was adjusted to 1.

C. K Addition

Pd—Ti catalyst was impregnated in 100 ml aqueous solution of 0.02% by weight $KNO_3$, and the catalyst was then dried at 100° C. for 3 hours and calcinated in air at 300° C. for 2 hours. The atomic ratio of K/Pd was adjusted to 0.1.

D. Reduction

The catalyst samples were flushed with $N_2$ to remove $O_2$, and then reduced in $H_2$ at 300° C. for 2 hours. Consequently, the catalyst was prepared with the atomic ratio of K/Ti/Pd was adjusted to 0.1/1/1.

Example 2

Comparative—Catalyst B

Pd catalyst was prepared using the same method as in Example 1, except for Ti addition (Step B) and K addition (Step C). That is, 1% by weight Pd catalyst by impregnating Pd on silica was prepared (Step A), and reduced in $H_2$ at 300° C. for 1 hour (Step D).

Example 3

Comparative—Catalyst C

Pd—Ti catalyst was prepared using the same method as in Example 1, except for K addition (Step C). That is, 1% by weight Pd catalyst by impregnating Pd on silica was prepared (Step A), Pd—Ti catalyst by Ti addition with the atomic ratio of Pd/To of 1 was prepared (Step B), and reduced in $H_2$ at 300° C. for 1 hour (Step D).

Example 4

Comparative—Catalyst D

Pd—Ti catalyst was prepared using the same method as in Example 3, except that the catalyst was reduced at 500° C.

Example 5

Chemisorption Experiment

Chemisorption experiment was performed to investigate the amount of CO chemisorbed on the catalyst surface.

Catalysts A-D were pressed into a self-supporting disc, placed in an iR cell, reduced in $H_2$, and then absorbed $H_2$ was removed by evacuation. IR cell was cooled to 40° C., and then the catalyst was exposed to CO. The IR spectra of adsorbed CO were recorded after removing gaseous CO from the cell by evacuation. The amounts of CO chemisorbed and the chemisorption behaviour of the catalysts are summarized in Table 1.

TABLE 1

| Sample | Component | Reduction Temp. (° C.) | CO/Pd | $A_l/A_m$ [a] |
|---|---|---|---|---|
| Catalyst B | Pd | 300 | 0.76 | 0.31 |
| Catalyst C | Pd—Ti | 300 | 0.63 | 0.37 |
| Catalyst D | Pd—Ti | 500 | 0.28 | 0.77 |
| Catalyst A | Pd—Ti—K | 300 | 0.26 | 1.39 |

[a] Area ratio of a linearly-bound CO to a multiply-bound CO

When the catalysts are reduced at 300° C., the difference between the amounts of CO adsorbed on Pd—Ti catalyst (Catalyst C) and on Pd catalyst (Catalyst B) is not significant. The amounts of CO adsorbed is drastically decreased when the Pd—Ti catalyst is reduced at 500° C. (catalyst D), and the area ratio of linearly-bound $CO(A_l)$/multiply-bound $CO(A_m)$ is increased.

The reason for why the $A_l/A_m$ ratio is increased whereas total quantity of adsorbed CO decreased is because Ti species migrated on to the Pd surface and modified the surface.

In the case of Pd—Ti—K catalyst (Catalyst A), the amount of adsorbed CO is decreased and the area ratio of linearly-bound $CO(A_l)$/multiply-bound $CO(A_m)$ is high even though the catalyst is reduced at a lower temperature, 300° C.

Example 6

XPS Experiments

The concentration of Ti and Pd on the catalyst surface before and after reduction was investigated by XPS analyses.

Catalysts A, C and D were reduced, protected from air oxidation by wetting the surface with isooctane, mounted on a double-sided adhesive tape, and then placed in UHV chamber for XPS analysis.

Table 2 shows the area ratios of Ti/Pd on the catalyst surface before and after reduction.

TABLE 2

| Sample | Component | $Ti_{2p}/Pd_{3d}$ ratio before reduction | $Ti_{2p}/Pd_{3d}$ ratio after reduction |
|---|---|---|---|
| Catalyst C | Pd—Ti | 1.15 | 1.16 |
| Catalyst D | Pd—Ti | 1.15 | 1.37 |
| Catalyst A | Pd—Ti—K | 1.43 | 2.04 |

The Ti/Pd ratio of Pd—Ti catalyst reduced at 500° C. (Catalyst D) is higher than that of Pd—Ti catalyst reduced at 300° C. (Catalyst C) due to the decoration of the Pd surface with Ti species. The Ti/Pd ratio of Pd—Ti—K catalyst is remarkably increased even after reduction at a lower temperature, 300° C.

Example 7

Acetylene Hydrogenation Reaction

Ethylene selectivity for selective hydrogenation of acetylene of Catalysts A-D is investigated.

A. Reaction Gas

Gas mixture containing 1.02% by volume of acetylene in ethylene.

B. Experiments

Acetylene hydrogenation was performed in a pyrex microreactor with ¼ inch diameter using 0.03 g catalysts. The flow rate of the reactant mixture was varied at 400, 800, 1200, 1600, 2000, and 2400 ml/min. Mole ratio of $H_2$/acetylene was 2, and experiments were conducted at 60° C.

C. Results

Figure 1:
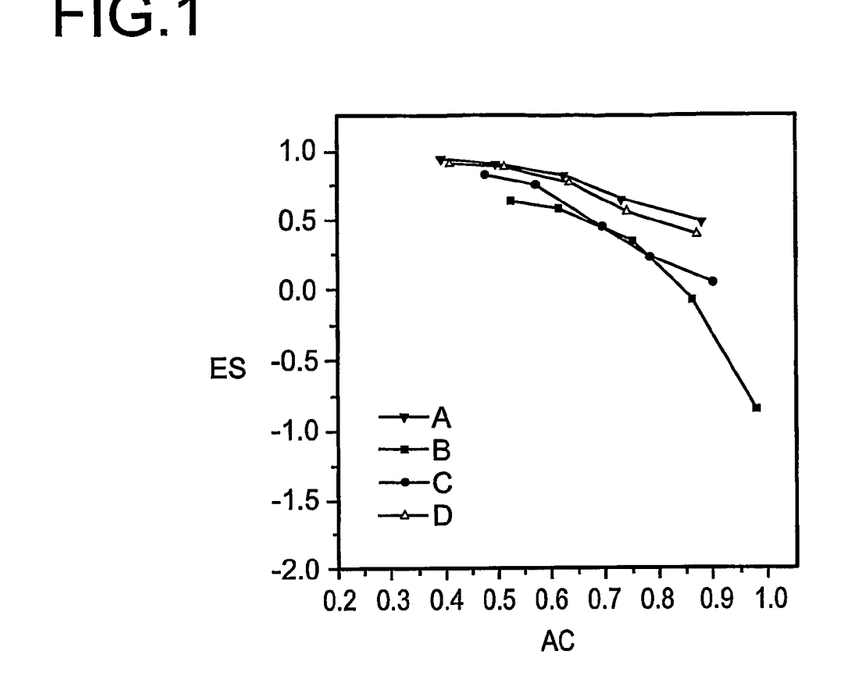
FIG. 1 illustrates acetylene conversion and ethylene selectivity.

Acetylene conversion and ethylene selectivity, calculated by the following equations, were shown in FIG. 1. In FIG. 1 ES means ethylene selectivity, AC means acetylene conversion, A means catalyst A, B means catalyst B, C means catalyst C and D means catalyst D.

Acetylene conversion=$A/A_0$     [Equation 1]

Ethylene selectivity=$\Delta B/\Delta A$     [Equation 2]

In the above equations, $A_0$ represents the initial concentration of acetylene in the feed, $\Delta A$ represents a change in the acetylene concentration, and $\Delta B$ represents a change in the ethylene concentration.

When the Pd—Ti catalyst is reduced at 300° C. (Catalyst C), the ethylene selectivity curve of Catalyst C nearly overlaps that of Pd catalyst reduced at 300° C. (Catalyst B). However, when the Pd—Ti catalyst is reduced at 500° C. (Catalyst D), the ethylene selectivity increased, suggesting that the ethylidyne production which needs multiply-bound adsorption sites is suppressed due to the modification of the Pd surface by Ti species.

In the case of Pd—Ti—K catalyst, the ethylene selectivity is higher than that of Pd—Ti catalyst reduced at 500° C. (Catalyst D), even though the Pd—Ti—K catalyst is reduced at 300° C. (Catalyst A). This results from the formation of potassium titanate by the reaction of $K_2O$ and $TiO_2$. Potassium titanate has a significantly lower melting point, that is a lower Tammann temperature, than titania, therefore, it effectively modifies the Pd surface even after reduction at a low temperature, 300° C. The trend of reaction tests is in accordance with that of XPS results.

Example 8

In Accordance with the Invention—Catalyst E-H

Pd—Ti—K catalysts were prepared using the same method as in Example 1, except for the mole ratio of KlTi/Pd, which was 0.01/1/1 (Catalyst E), 1/1/1 (Catalyst F), 4/1/1 (Catalyst G), and 10/1/1 (Catalyst H).

Example 9

Acetylene Hydrogenation Reaction

Figure 2:
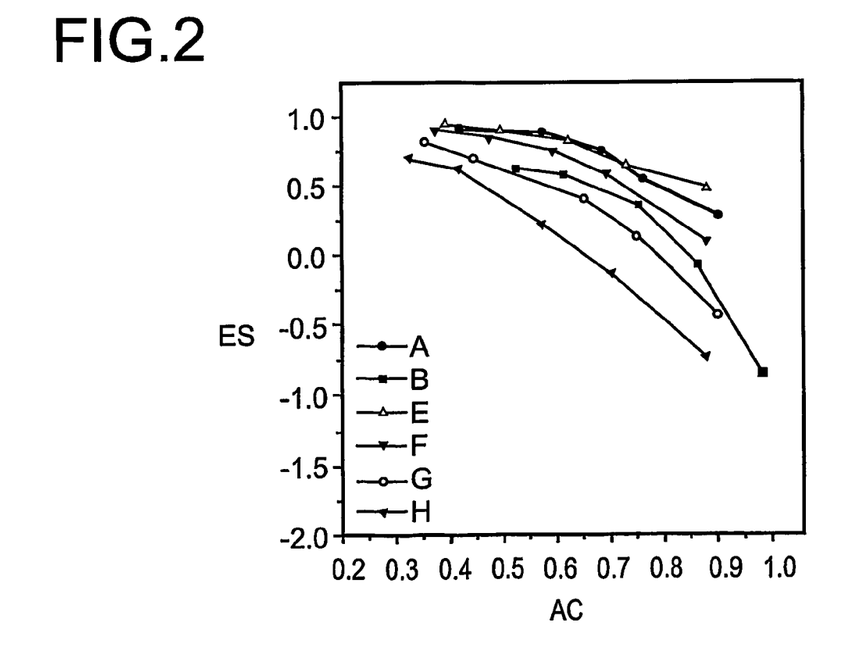
FIG. 2 illustrates the effect of the amounts of added K on the ethylene selectivity.

To investigate the effect of the amounts of added K on the ethylene selectivity, the experiments were conducted under the same condition as in Example 7 using Catalyst A, E-H. The reaction results are plotted in FIG. 2. In FIG. 2 ES means ethylene selectivity, AC means acetylene conversion, A means catalyst A, B means catalyst B, E means catalyst E, F means catalyst F, C means catalyst G and H means catalyst H.

As the amount of K increases, the ethylene selectivity is increased until the ratio of K/Pd is 0.1 (Catalyst A), and then is decreased as the amount of added K increases to above certain amounts (Catalyst E-H). The existence of the excessive K increases the formation of oligomer such as 1,3-butadiene and consequently, degrades the activity and selectivity of a catalyst. The optimal ratio of K/Pd is 0.1 (Catalyst A).

According to the present invention, Pd—Ti—K catalyst has very high ethylene selectivity over a wide range of conversion even after reduction at a low temperature, 300° C.

Example 10

In Accordance with the Invention—Catalyst I

A. Preparation of Pd catalyst $Pd/SiO_2$ catalyst was prepared by a literature method. 20 g of Silica (JRC-SIO-6, BET surface area: 109 $m^2/g$) were impregnated with 200 ml solution of 0.33% by weight $Pd(NH_3)_4(OH)_2$ and the solution was stirred for 12 hours, and centrifuged and washed with distilled water. The catalyst was then dried at 100° C. for 12 hours and calcined in air at 300° C. for 2 hours. 1% by weight $Pd/SiO_2$ catalyst was obtained.

B. La Addition

La-modified Pd catalysts were prepared by incipient wetness impregnation method. 1% by weight $Pd/SiO_2$ was impregnated with 3 ml of 2% by weight lanthanum nitrate hydrate $(La(NO_3)_3 \cdot xH_2O)$ aqueous solution. The catalyst was then dried at 100° C. for 6 hours and calcinated in air at 300° C. for 2 hours.

C. Pre-Reduction and Si Deposition 3 g of Pd—La catalyst was placed in a fixed bed reactor, reduced in $H_2$ at 500° C. for 1 hour, cooled to 250° C. in $N_2$ flowing. The catalyst was exposed to 1% $SiH_4/Ar$ by pulse through the 0.01 ml sampling loop, while the amounts of Si addition were controlled by the number of pulse injection. $H_2$ was used as a carrier gas at a rate of 20 ml/min. And then the catalyst was exposed to $O_2$ at 25° C. for 2 hours.

D. Reduction

The catalyst samples were reduced in $H_2$ at 300° C. for 1 hour. Consequently, the Pd—Si catalyst was prepared with the atomic ratio of Si/Pd adjusted to 0.012.

Example 11

In Accordance with the Invention—Catalyst J

The catalyst was prepared using the same method as in Example 10, except that the mole ratio of Si/Pd was 0.006.

Example 12

In Accordance with the Invention—Catalyst K

The catalyst was prepared using the same method as in Example 10, except that the mole ratio of Si/Pd was 0.12.

Example 13

Comparative—Catalyst L

The catalyst was prepared using the same method as in Example 2, however, the catalyst was reduced at 500° C.

Example 14

Comparative—Catalyst M

The catalyst was prepared using the same method as in Example 10, except for Si addition (Step C). That is, 1% by weight Pd catalyst was prepared (Step A), Pd—La catalyst was prepared with the La/Pd ratio of 1 (Step B), and reduced in $H_2$ at 300° C. for 1 hour (Step D).

Example 15

Comparative—Catalyst N

The catalyst was prepared using the same method as Example 14, however, the catalyst was reduced at 500° C.

Example 16

Acetylene Hydrogenation Reaction

Ethylene selectivity for selective hydrogenation of acetylene of catalyst I, B, L-N was investigated.

A. Reaction Gas

Gas mixture containing 1.02% by volume of acetylene in ethylene.

B. Experiments

Acetylene hydrogenation was performed in a pyrex microreactor with ¼ inch diameter using 0.03 g catalysts. The flow rate of the reactant mixture was varied at 400, 800, 1200, 1600, 2000, and 2400 ml/min. Mole ratio of $H_2$/acetylene was 2, and experiments were conducted at 60° C.

C. Results

Figure 3:
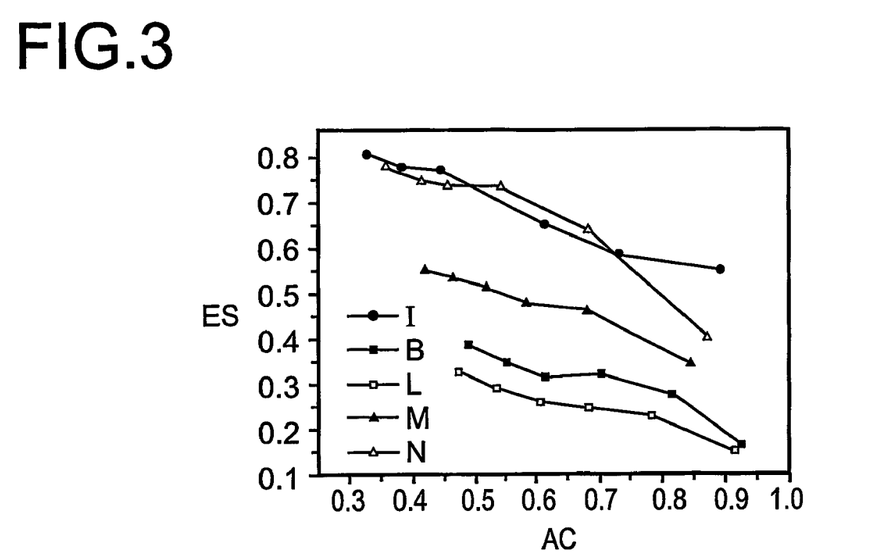
FIG. 3 illustrates acetylene conversion and ethylene selectivity.

Acetylene conversion and ethylene selectivity, calculated by the following equations are shown in FIG. 3. In FIG. 3 ES means ethylene selectivity, AC means acetylene conversion, I means catalyst I, B means catalyst B, L means catalyst L, M means catalyst M and N means catalyst N.

Acetylene conversion=$A/A_0$  [Equation 1]

Ethylene selectivity=$\Delta B/\Delta A$  [Equation 2]

In the above equations, $A_0$ represents the initial concentration of acetylene in the feed, $\Delta A$ represents a change in the acetylene concentration, and $\Delta B$ represents a change in the ethylene concentration.

The ethylene selectivity of Pd—La catalyst reduced at 300° C. (Catalyst M) is a little higher than that of Pd catalyst reduced at 300° C. (Catalyst B). However, when Pd—La catalyst is reduced at 500° C. (Catalyst N), the ethylene selectivity is improved significantly compared to that of Pd—La (Catalyst M) and Pd catalyst (Catalyst B) reduced at 300° C. On the other hand, the ethylene selectivity of Pd catalyst reduced at 500° C. (Catalyst L) is very low due to the sintering of Pd particles. The high ethylene selectivity of Pd—La catalyst reduced at 500° C. (Catalyst N) originates from the Strong Metal-Support Interaction (SMSI) between La and Pd. La species modifies Pd surface, such that reduces the ethane production by suppressing the ethylidyne formation which needs multiply-bound adsorption sites and also suppresses the 1,3-butadiene production which causes catalyst deactivation, and consequently, the ethylene selectivity is increased.

On the other hand, the reason for why the ethylene selectivity of Pd—La catalyst reduced at 300° C. (Catalyst M) is lower than that of Pd—La catalyst reduced at 500° C. (Catalyst N) is because Pd surface is not modified sufficiently by La species due to the low reduction temperature.

The ethylene selectivity of Pd—La—Si catalyst reduced at 300° C. (Catalyst I) is higher than that of Pd—La catalyst reduced at 300° C. (Catalyst M) although the catalyst is reduced at a low temperature, and is similar to that of Pd—La catalyst reduced at 500° C. (Catalyst N). This indicates that the improved catalytic performance of Pd—La catalyst reduced at 500° C. can be maintained by Si addition, although the catalyst is reduced at low temperatures after exposure to $O_2$ during the catalyst regeneration. We concluded that the Si species effectively anchors La on the Pd surface to some extents.

Example 17

Acetylene Hydrogenation

Figure 4:
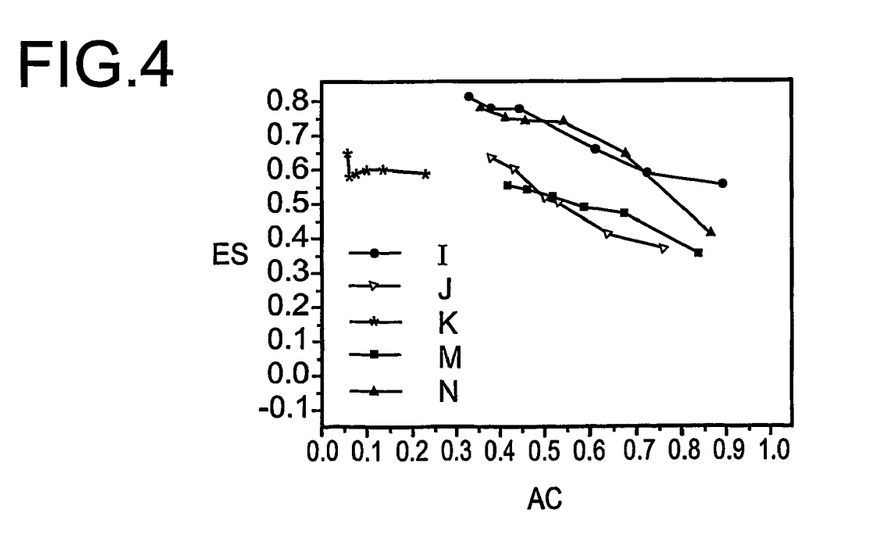
FIG. 4 illustrates the effect of the amounts of added Si on the ethylene selectivity.

To investigate the effect of the amounts of added Si on the ethylene selectivity, the experiments were conducted under the same condition as in Example 16 using the Catalyst I-K, M and N. The reaction results are plotted in FIG. 4. In FIG. 4 ES means ethylene selectivity, AC means acetylene conversion, I means catalyst I, J means catalyst J, K means catalyst K, M means catalyst M and N means catalyst N.

When the Si/Pd ratio is 0.006 and reduced at 300° C. (Catalyst J), the ethylene selectivity of the Pd—La—Si is almost the same as that of Pd of Pd—La—Si catalyst reduced at 300° C. (catalyst M). But, as the Si/Pd ratio increases up to 0.012, and reduced at 300° C. (Catalyst I), the ethylene selectivity of the Pd—La—Si is increased to the level of Pd—La catalyst reduced at 500° C. (Catalyst N). When an excess amount of Si is deposited i.e. the Si/Pd ratio, and reduced at 300° C. (Catalyst K), the ethylene selectivity as well as the acetylene conversion is decreased. In the case of Catalyst J with the Si/Pd ratio of 0.006, the amount of silicon is so small that it cannot anchor the lanthanum effectively, and vice versa, in the case of Catalyst K with the Si/Pd ratio of 0.12, the amount of silicon is so large that it can cover most of the active sites, consequently, both the conversion and the selectivity is decreased significantly. Accordingly, the optimal Si/Pd ratio to obtain an elevated selectivity while maintaining a relatively high acetylene conversion exists and is 0.012 under this experimental condition.

According to the present invention, Pd—La—Si catalyst has very high ethylene selectivity, which is comparable to that of Pd—La catalyst reduced at 500° C., in the wide ranges of conversion even after reduction at a low temperature, 300° C.

Example 18

In Accordance with the Invention—Catalyst O

A. Preparation of Pd Catalyst

Pd/$SiO_2$ catalyst was prepared by a literature method. 20 g of Silica (JRC-SIO-6, BET surface area: 109 $m^2$/g) were impregnated with 200 ml solution of 0.33% by weight Pd($NH_3$)$_4$(OH)$_2$ and the solution was stirred for 12 hours, and centrifuged and washed with distilled water. The catalyst was then dried at 100° C. for 12 hours and calcined in air at 300° C. for 2 hours, 1% by weight Pd/$SiO_2$ catalyst was obtained.

B. Nb Addition

Nb-modified Pd catalysts were prepared by wet impregnation method. 1% by weight Pd/$SiO_2$ was impregnated with tetrakis niobium dissolved hexane solution. The catalyst was then dried at 100° C. for 6 hours and calcined in air at 300° C. for 2 hours.

C. Reduction

The catalyst samples were flushed with $N_2$ to remove $O_2$, and then reduced in $H_2$ at 300° C. for 2 hours. Consequently, the Pd—Nb catalyst was prepared with the atomic ratio of Nb/Pd was adjusted to 1.

Example 19

Comparative—Catalyst P

Pd—Nb catalysts were prepared using the same method as in Example 18, except that the catalyst was reduced at 500° C.

Example 20

Chemisorption Experiment

Chemisorption experiment was performed to investigate the amount of $H_2$ chemisorbed on the catalyst surface. Catalysts O, P, B, L were pressed into a self-supporting disc, placed in an IR ell, reduced in $H_2$, and then absorbed $H_2$ was removed by evacuation. IR cell was cooled to 40° C., and then the catalyst was exposed to $H_2$. The IR spectra of adsorbed $H_2$ were recorded after removing gaseous $H_2$ from the cell by evacuation. The amounts of $H_2$ chemisorbed and the chemisorption behaviour on the catalysts are summarized in Table 3.

TABLE 3

| Sample | Component | Reduction Temp. (° C.) | H/Pd |
|---|---|---|---|
| Catalyst B | Pd | 300 | 0.48 |
| Catalyst L | Pd | 500 | 0.32 |
| Catalyst O | Pd—Nb | 300 | 0.22 |
| Catalyst P | Pd—Nb | 500 | 0.17 |

On Pd catalyst, the amount of $H_2$ uptake decreases due to the sintering of Pd particles when the reduction temperature is raised from 300° C. (Catalyst B) to 500° C. (Catalyst L). Pd—Nb catalyst reduced at 500° C. (Catalyst P) also exhibits much decrease in the amount of chemisorbed $H_2$ than that of Pd catalyst reduced at 500° C. (Catalyst L), due to the decoration of Pd surface with Nb species. This is a typical phenomenon of SMSI, which occurs when the Pd—Nb catalyst is reduced at high temperatures.

The amount of $H_2$ uptake on Pd—Nb catalyst reduced at 300° C. (Catalyst O) is also remarkably reduced and this value is almost the same as that of Pd—Nb catalyst reduced at 500° C. (Catalyst P), which indicates that the strong interaction between Pd and Nb exists even after a reduction at low temperature, e.g., 300° C. Therefore, if we use Nb as a promoter, we can effectively modify Pd surface at relatively low temperatures.

Example 21

Acetylene Hydrogenation Reaction

Ethylene selectivity for selective hydrogenation of acetylene of Catalyst O, P, B, L was investigated.

A. Reaction gas

Gas mixture containing 1.02% by volume of acetylene in ethylene.

B. Experiments

Acetylene hydrogenation was performed in a pyrex microreactor with ¼ inch diameter using 0.03 g catalysts. The flow rate of the reactant mixture was varied at 400, 800, 1200, 1600, 2000, and 2400 ml/min. Mole ratio of $H_2$/acetylene was 2, and experiments were conducted at 60° C.

C. Results

Figure 5:
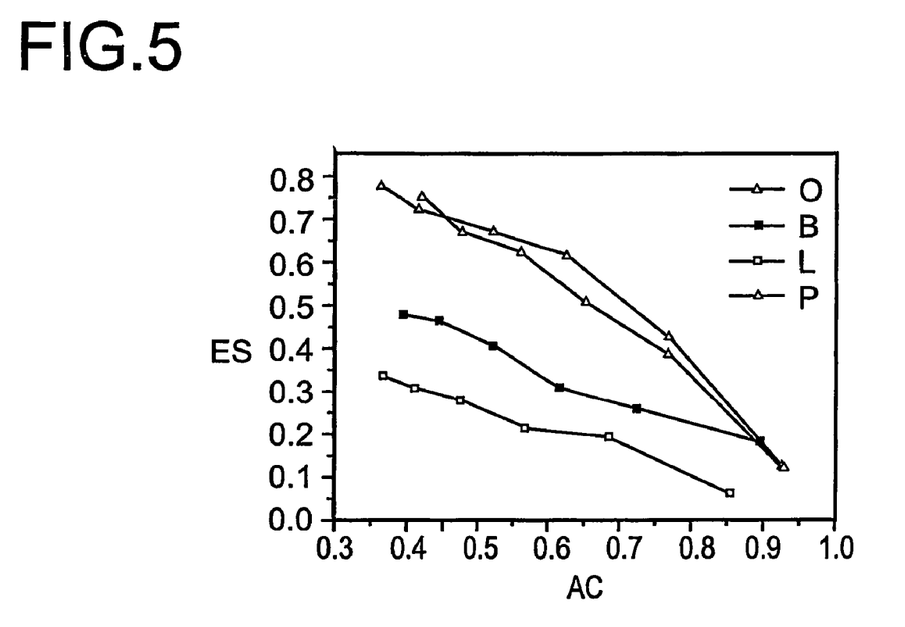
FIG. 5 illustrates acetylene conversion and ethylene selectivity.

Acetylene conversion and ethylene selectivity, calculated by the following equations, are shown in FIG. 5. In FIG. 5 ES means ethylene selectivity, AC means acetylene conversion, O means catalyst O, B means catalyst B, L means catalyst L and P means catalyst P.

$$\text{Acetylene conversion} = A/A_0 \qquad [\text{Equation 1}]$$

$$\text{Ethylene selectivity} = \Delta B/\Delta A \qquad [\text{Equation 2}]$$

In the above equations, $A_0$ represents the initial concentration of acetylene in the feed, $\Delta A$ represents a change in the acetylene concentration, and $\Delta B$ represents a change in the ethylene concentration.

The ethylene selectivities of Pd—Nb catalysts (Catalyst O, P) are higher than those of Pd catalysts (Catalyst B, L) irrespective of reduction temperatures. In the case of Pd catalyst reduced at 500° C. (Catalyst P), Pd particles are sintered, resulting in the formation of multiply-coordinated Pd sites, which accelerates 1,3-butadiene formation, consequently, the ethylene selectivity is lowered.

Compared to the Ti promoter, presented in previous examples, the ethylene selectivity of Pd—Nb catalyst reduced at 300° C. (Catalyst O) is almost the same as that of Pd—Nb catalyst reduced at 500° C. (Catalyst P), which indicates that Nb promoter strongly reacts with Pd even after reduction at low temperatures.

That is, Nb effectively modifies Pd surface even after reduction at low temperatures, suppresses the multiply-coordinated Pd sites, which is responsible for the ethane formation via ethyldine and green oil formation via 1,3-butadiene production, consequently, increases the ethylene selectivity.

According to the present invention, Pd—Nb catalyst has very high ethylene selectivity over a wide range of conversion even after reduction at low temperatures.

Example 22

In Accordance with the Invention—Catalyst Q

A. Preparation of Pd Catalyst

Pd/$SiO_2$ catalyst was prepared by a literature method. 20 g of Silica (JRC-SIO-6, BET surface area: 109 $m^2$/g) were impregnated with 200 ml solution of 0.33% by weight $Pd(NH_3)_4(OH)_2$ and the solution was stirred for 12 hours, and centrifuged and washed with distilled water. The catalyst was then dried at 100° C. for 12 hours and calcined in air at 300° C. for 2 hours. 1% by weight Pd/$SiO_2$ catalyst was obtained.

B. La Addition

La-modified Pd catalysts were prepared by incipient wetness impregnation method. 1% by weight Pd/$SiO_2$ was impregnated with 3 ml of 2% by weight lanthanum nitrate hydrate $(La(NO_3)_3 \cdot xH_2O)$ aqueous solution. The catalyst was then dried at 100° C. for 6 hours and calcined in air at 300° C. for 2 hours.

C. Reduction

The catalyst samples were flushed with $N_2$ to remove $O_2$, and then reduced in $H_2$ at 500° C. for 2 hours. Consequently, the Pd—La catalyst was prepared with the atomic ratio of La/Pd adjusted to 1.

Example 23

Comparative—Catalysts R, S, T

Pd catalyst was prepared using the same method as Example 23 (Step A), and La species was added to Pd catalyst (Step B). The reduction in Step C was conducted at 300° C. (Catalyst R), 400° C. (Catalyst S), and 450° C. (Catalyst T). The atomic ratio of La/Pd was adjusted to 1 in the three catalysts.

Example 24

Chemisorption Experiment

Chemisorption experiment was performed to investigate the amount of CO chemisorbed on the catalyst surface.

Catalysts B, Q-T were pressed into a self-supporting disc, placed in an IR cell, reduced in $H_2$, and then adsorbed $H_2$ was removed by evacuation. IR cell was cooled to 40° C., and then the catalyst was exposed to CO. The IR spectra of adsorbed CO were recorded after removing gaseous CO from the cell by evacuation. The amounts of CO chemisorbed and the chemisorption behaviour on the catalysts was summarized in Table 4.

TABLE 4

| Sample | Component | Reduction Temp. (° C.) | CO/Pd | $A_l/A_m$[a] |
|---|---|---|---|---|
| Catalyst B | Pd | 300 | 0.70 | 1.31 |
| Catalyst R | Pd—La | 300 | 0.45 | 3.18 |

TABLE 4-continued

| Sample | Component | Reduction Temp. (° C.) | CO/Pd | $A_l/A_m$[a] |
|---|---|---|---|---|
| Catalyst S | Pd—La | 400 | 0.38 | 3.23 |
| Catalyst T | Pd—La | 450 | 0.09 | 6.89 |
| Catalyst Q | Pd—La | 500 | 0.04 | 7.14 |

[a]Area ratio of a linearly-bound CO to a multiply-bound CO.

When the catalysts are reduced at 300° C., the difference between the amounts of CO adsorbed on Pd—La catalyst (Catalyst R) and on Pd catalyst (Catalyst B) is not significant. The amount of adsorbed CO is decreased with an increase in the reduction temperature, drastically decreasing at temperatures above 450° C. (Catalyst T, Catalyst Q), and the area ratio of linearly-bound $CO(A_l)$/multiply-bound $CO(A_m)$ is increased.

The fact that the $A_l/A_m$ ratio increases significantly whereas the total amount of adsorbed CO decreases indicates that Pd and La species interact strongly with each other after reduction at temperatures above 450° C., so that, La species migrated onto the Pd surface and partially modify the Pd surface. The extent of this modification effect is greatest when the catalyst is reduced at 500° C.

Example 25

Acetylene Hydrogenation Reaction

Ethylene selectivity for selective hydrogenation of acetylene of Catalyst Q-T, B was investigated.

A. Reaction Gas

Gaseous mixture containing 1.02% by volume of acetylene in ethylene was used.

B. Experiments

Acetylene hydrogenation was performed in a pyrex micro-reactor with ¼ inch diameter using 0.03 g catalysts. The flow rate of the reactant mixture was varied at 400, 800, 1200, 1600, 2000, and 2400 ml/min. Mole ratio of $H_2$/acetylene was 2, and experiments were conducted at 60° C.

C. Results

Figure 6:
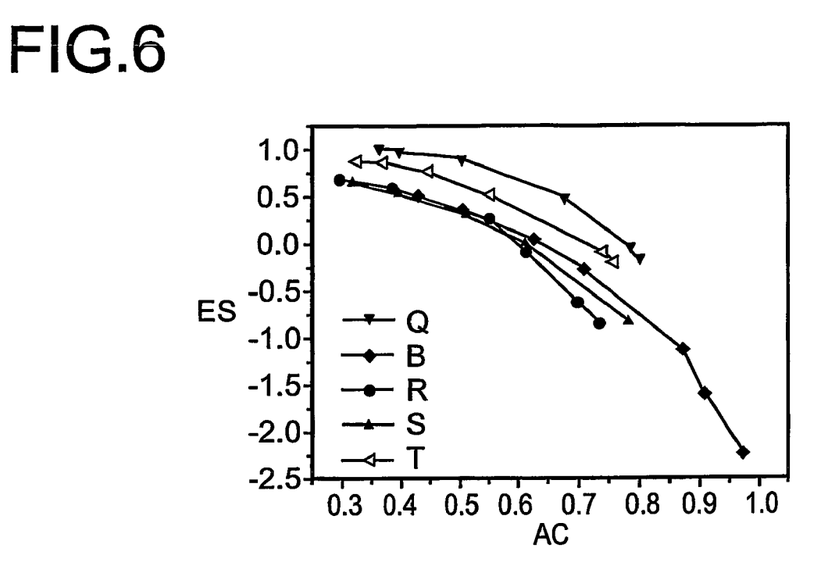
FIG. 6 illustrates acetylene conversion and ethylene selectivity.

Acetylene conversion and ethylene selectivity, calculated by the following equations, are shown in FIG. 6. In FIG. 6 ES means ethylene selectivity, AC means acetylene conversion, Q means catalyst Q, B means catalyst B, R means catalyst R, S means catalyst S and T means catalyst T.

$$\text{Acetylene conversion} = A/A_0 \qquad [\text{Equation 1}]$$

$$\text{Ethylene selectivity} = \Delta B/\Delta A \qquad [\text{Equation 2}]$$

In the above equations, $A_0$ represents the initial concentration of acetylene in the feed, $\Delta A$ represents a change in the acetylene concentration, and $\Delta B$ represents a change in the ethylene concentration.

The ethylene selectivity of Pd—La catalyst reduced at 300° C. (Catalyst R) and at 400° C. (Catalyst S) is similar to that of Pd catalyst reduced at 300° C. (Catalyst B). As the reduction temperature increases to a value higher than 450° C., the ethylene selectivity increases (Catalyst T and Catalyst Q), and that of Pd—La catalyst reduced at 500° C. (Catalyst Q) increases up to 98%. This value is 10% higher than that of Pd—Ti catalyst, the results of which was presented in the previous examples.

The high ethylene selectivity of Pd—La catalyst reduced at 500° C. (Catalyst Q) originates from the Strong Metal-Support Interaction (SMSI) between La and Pd. La species modifies Pd surface, such that the species reduces the ethane production by suppressing the ethylidyne formation which needs multiply-bound adsorption sites and also suppresses the production of 1,3-butadiene which causes catalyst deactivation. Consequently, the ethylene selectivity is increased. On the other hand, the reason for why the ethylene selectivity of Pd—La catalyst reduced at temperatures below 400° C. (Catalyst R and Catalyst S) is lower than that of Pd—La catalyst reduced at 500° C. (Catalyst Q) is because Pd surface has not been sufficiently modified by La species at relatively low temperatures.

Example 26

In Accordance with the Invention—Catalysts U-X

Pd—La catalysts were prepared by using the same method as in Example 22, except for the mole ratio of La/Pd, which was 0.5/1 (Catalyst U), 0.75/1 (Catalyst V), 1.5/1 (Catalyst W), and 2/1 (Catalyst X).

Example 27

Acetylene Hydrogenation Reaction

Figure 7:
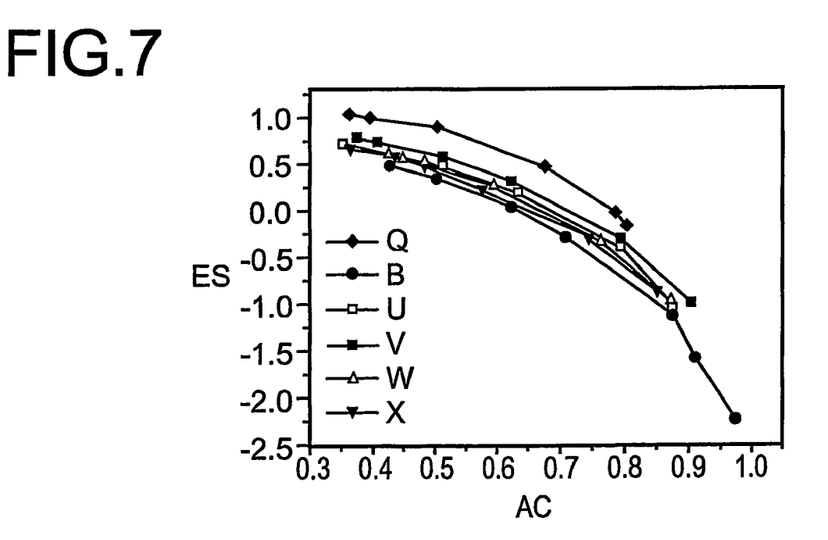
FIG. 7 illustrates acetylene conversion and ethylene selectivity.

To investigate the effect of the amounts of added La on the ethylene selectivity, the experiments were conducted under the same condition as in Example 24 using Catalyst Q, U-X and B. The reaction results are plotted in FIG. 7. In FIG. 7 ES means ethylene selectivity, AC means acetylene conversion, Q means catalyst Q, B means catalyst B, U means catalyst U, V means catalyst V, W means catalyst W and X means catalyst X.

As the amounts of La increases, the ethylene selectivity is increased until the ratio of La/Pd is 1 (Catalyst R), and then is decreased to the level of Pd catalyst (Catalyst B), when the ratio of La/Pd is 2/1 (Catalyst X). When the La/Pd ratio is smaller than 1 (Catalyst U, V), the catalytic performance is not improved significantly because the La species cannot effectively decorate Pd surface although the reduction temperature is sufficiently high. When La/Pd ratio is larger than 1 (Catalyst W, X), the La species decorate Pd surface too much, such that the catalytic activity is lowered. Therefore, it is concluded that there is an optimum La/Pd ratio which permits the La species to effectively modify the Pd surface, and that the ratio is 1 (Catalyst Q) under the above-experimental condition.

Example 28

Deactivation Tests

To study the deactivation behaviour of the catalysts, deactivation tests were conducted under the following conditions using Catalysts Q and B. (The reaction condition was severer than those in Example 25 and 27 such that catalysts were deactivated at higher rates.)

A. Reaction Gas.

The reactant stream contained 4.84% by volume of acetylene in ethylene.

B. Experiments

Deactivation tests were performed in a pyrex micro-reactor of ¼ inch diameter using 0.05 g catalysts. The flow rate of the reactant mixture was 400 ml/min. Molar ratio of $H_2$/acetylene was 1, and experiments were conducted at 90° C.

C. Results

Figure 8:
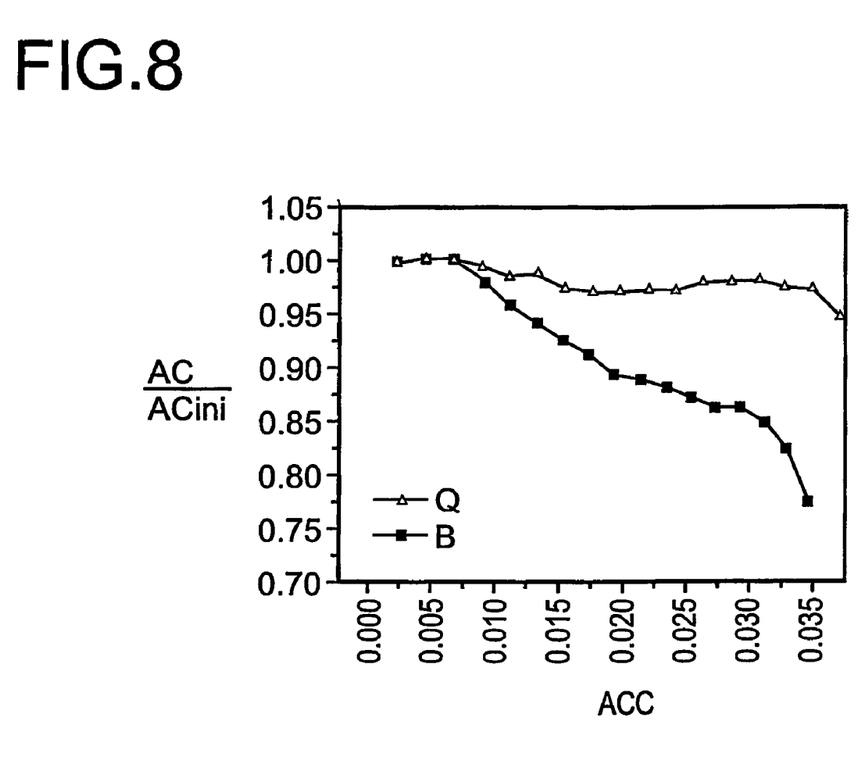
FIG. 8 illustrates $AC/AC_{(Ini)}$ means acetylene conversion/acetylene conversion (initial) and ACC means accumulated amount of converted acetylene (mol).

The results are plotted in FIG. 8. In FIG. 8 $AC/AC_{(ini)}$ means acetylene conversion/acetylene conversion (initial), ACC means accumulated amount of converted acetylene (mol), Q means catalyst Q and B means catalyst B. In order to compare the deactivation behaviours of Pd and Pd—La catalysts, we have plotted the normalized acetylene conversion versus the accumulated amount of converted acetylene instead of plotting versus the time-on-stream, such that the comparison is made based on the same load of the reaction. The deactivation rate of Pd catalyst reduced at 300° C. (Catalyst B) was much higher than that of Pd—La catalyst reduced at 500° C. (Catalyst Q).

Also, as shown in Table 5, green oil was produced in smaller amounts on Pd—La catalyst reduced at 500° C. (Catalyst Q) than on Pd catalyst reduced at 300° C. (Catalyst B). As mentioned in the above Example 5, the reason for why Pd—La catalyst reduced at 500° C. (Catalyst Q) is slowly deactivated is because the La species effectively modify the Pd surface when the catalyst is reduced at high temperatures. The La species suppress the production of 1,3-butadiene, which deactivates catalysts.

TABLE 5

| Sample | % by weight of green oil on a deactivated catalyst |
| --- | --- |
| Pd—La catalyst (Catalyst Q) | 41.1 |
| Pd catalyst (Catalyst B) | 55.5 |

According to the present invention, the Pd—La catalyst has very high ethylene selectivity over a wide range of conversion, and retards the catalyst deactivation by suppressing the formation of 1,3-butadiene in the selective hydrogenation of acetylene. Therefore, Pd—La catalyst has an advantage in an economical aspect in a sense that it extends the catalyst regeneration cycle.

The invention claimed is:

1. A palladium catalyst consisting of a support and
   from 0.05 to 2.0% by weight, based on the supported catalyst, of palladium and from 0.035 to 5.2% by weight, based on the supported catalyst, of lanthanum,
   or
   from 0.05 to 2.0% by weight, based on the supported catalyst, of palladium, from 0.02 to 1.0% by weight, based on the supported catalyst, of titanium and from 0.0002 to 7.4% by weight, based on the supported catalyst, of potassium,
   or
   from 0.05 to 2.0% by weight, based on the supported catalyst, of palladium, from 0.035 to 5.2% by weight, based on the supported catalyst, of lanthanum and from 0.0001 to 0.065% by weight, based on the supported catalyst, of silicon,
   wherein the rest of the catalyst is the support.

2. The palladium catalyst as claimed in claim 1, which consists of a support and from 0.05 to 2.0% by weight, based on the supported catalyst, of palladium and from 0.035 to 5.2% by weight, based on the supported catalyst, of lanthanum, wherein the rest of the catalyst is the support.

3. The palladium catalyst as claimed in claim 1, which consists of a support and
   from 0.05 to 2.0% by weight, based on the supported catalyst, of palladium, from 0.02 to 1.0% by weight, based on the supported catalyst, of titanium and from 0.0002 to 7.4% by weight, based on the supported catalyst, of potassium,
   wherein the rest of the catalyst is the support.

4. The palladium catalyst as claimed in claim 1, which consists of a support and
   from 0.05 to 2.0% by weight, based on the supported catalyst, of palladium, from 0.035 to 5.2% by weight, based on the supported catalyst, of lanthanum and from 0.0001 to 0.065% by weight, based on the supported catalyst, of silicon,
   wherein the rest of the catalyst is the support.

5. A process for preparing a palladium catalyst according to claim 1 which comprises impregnating a support in tetra amine palladium hydroxide aqueous solution followed by drying and calcination and impregnating the support with precursor solutions containing precursors of the further metals so as to obtain said palladium catalyst.

6. A process according to claim 5, wherein the Pd—La— or Pd—Ti—K-catalyst is prepared by impregnating the Pd-catalyst in corresponding precursor solution followed by drying and calcination.

7. A process according to claim 6, wherein a Pd—Ti—K-catalyst is prepared by impregnating a Pd—Ti-catalyst in potassium precursor solution followed by drying and calcination.

8. A process according to claim 5, wherein a Pd—La—Si-catalyst is prepared by Si-CVD on a Pd—La-catalyst, pre-reduced at 350 to 700° C., followed by oxidation at room temperature.

9. A process according to claim 5, wherein the producing of the catalysts includes the reduction process at 300 to 600° C. for 1 to 5 hours.

10. A process according to claim 5, wherein the La-precursor is lanthanum nitrate hydrate and the titanium precursors are chosen from a group consisting of $Ti(O-iPr)_2(DPM)_2$, titanium ethoxide, titanium oxide acetylacetonate and titanium butoxide.

11. A process according to claim 7, wherein the K-precursor is potassium nitrate.

12. A process according to claim 8, wherein the Si-precursor is selected from the group consisting of tetrahydrosilane, triethylsilane, tripropylsilane and phenylsilane.

13. A continuous process for the selective hydrogenation of acetylene to ethylene in the presence of a catalyst according to claim 1, wherein 0.5 to 2.0% by weight of acetylene in ethylene/acetylene gas mixture is used, the reaction temperature is 30 to 120° C. and the flow rate of the gas mixture is 200 to 2500 ml/min×g catalyst.

* * * * *